(12) United States Patent
Reinhardt et al.

(10) Patent No.: US 7,517,331 B2
(45) Date of Patent: Apr. 14, 2009

(54) ELASTIC KNEE-JOINT BANDAGE

(75) Inventors: Holger Reinhardt, Kempen (DE);
Heinrich Hess, Kleinblittersdorf (DE);
Hans B. Bauerfeind, Zeulenroda (DE);
Wolfgang Krause, Hofbieber (DE)

(73) Assignee: Bauerfeind AG, Zeulenroda (DE)

( * ) Notice: Subject to any disclaimer, the term of this patent is extended or adjusted under 35 U.S.C. 154(b) by 401 days.

(21) Appl. No.: 11/207,887

(22) Filed: Aug. 22, 2005

(65) Prior Publication Data

US 2006/0041214 A1 Feb. 23, 2006

(30) Foreign Application Priority Data

Aug. 23, 2004 (DE) .................. 10 2004 040 793

(51) Int. Cl.
*A61F 13/00* (2006.01)
*A61F 13/06* (2006.01)
*A61F 5/00* (2006.01)
*A41D 13/00* (2006.01)
*A41D 13/06* (2006.01)

(52) U.S. Cl. ............... 602/61; 602/5; 602/26; 602/60; 602/62; 2/22; 128/882

(58) Field of Classification Search ............ 2/16–24; 128/882, 892; 602/5, 23, 26, 61–63, 75–78; 606/212

See application file for complete search history.

(56) References Cited

U.S. PATENT DOCUMENTS

| 4,084,584 A | * | 4/1978 | Detty | 602/26 |
| 4,116,236 A | * | 9/1978 | Albert | 602/26 |
| 4,445,505 A | * | 5/1984 | Labour et al. | 602/26 |
| 5,334,135 A | * | 8/1994 | Grim et al. | 602/26 |
| 5,411,037 A | * | 5/1995 | Hess et al. | 128/882 |
| 5,474,524 A | * | 12/1995 | Carey | 602/26 |
| 5,730,710 A | | 3/1998 | Eichhorn et al. | |
| 6,149,616 A | | 11/2000 | Szlema et al. | |
| 6,287,269 B1 | * | 9/2001 | Osti et al. | 602/62 |
| 7,083,586 B2 | * | 8/2006 | Simmons et al. | 602/23 |
| 2003/0230121 A1 | * | 12/2003 | Yokoyama | 66/178 A |

FOREIGN PATENT DOCUMENTS

DE 34 16 231 A1 11/1985

(Continued)

*Primary Examiner*—Patricia M Bianco
*Assistant Examiner*—Keri J Nicholson
(74) *Attorney, Agent, or Firm*—Birch, Stewart, Kolasch & Birch, LLP

(57) ABSTRACT

Knee-joint bandage of elastic textile material, the knee-joint bandage being provided with a specially shaped insert surrounding the kneecap in a cutout. The specially shaped insert being covered by an overlay of identical or similar textile material attached to the textile material with the specially shaped insert being associated with a flexible, non-expandable tensioning member. The tensioning member connecting the regions of the kneecap poles on the fibula side in an arc around the kneecap such that, when the distance between the regions increases during bending of the knee joint, the distance of the arc from the connecting line between the kneecap poles is reduced and the tensioning member presses on the adjacent side of the kneecap, medially displacing and centering the latter, wherein the tensioning member is attached to the overlay in such a manner that, during bending of the knee joint and stretching of the overlay, the tensioning member displaces the kneecap.

5 Claims, 3 Drawing Sheets

FOREIGN PATENT DOCUMENTS

| | | |
|---|---|---|
| DE | 3416321 A1 | 11/1985 |
| DE | 3637879 A1 | 5/1988 |
| DE | 38 38 576 A1 | 5/1991 |
| DE | 90 17 540.9 U1 | 5/1991 |
| DE | 39 91 334 C1 | 7/1992 |
| DE | 93 16 342.8 U1 | 2/1994 |
| DE | 43 22 028 C2 | 1/1995 |
| DE | 295 19 978 U1 | 4/1996 |
| DE | 295 19 979 U1 | 4/1996 |
| DE | 200 05 661 U1 | 9/2001 |
| EP | 0 027 172 A1 | 4/1981 |
| EP | 0 360 277 A2 | 3/1990 |
| GB | 2279255 A * | 1/1995 |

* cited by examiner

ELASTIC KNEE-JOINT BANDAGE

The invention relates to a knee-joint bandage of elastic textile material, said knee-joint bandage being provided with a specially shaped insert surrounding the kneecap in a cutout, said specially shaped insert being covered by an overlay of identical or similar textile material attached to said textile material, the specially shaped insert being associated with a flexible, non-expandable tensioning member, said tensioning member connecting the regions of the kneecap poles on the fibula side in an arc around the kneecap such that, when the distance between said regions increases during bending of the knee joint, the distance of the arc from the connecting line between the kneecap poles is reduced and the tensioning member presses on the adjacent side of the kneecap, medially displacing and centering the latter.

Such a knee-joint bandage is described and presented in DE 38 38 576 A1. In the known knee-joint bandage, the tensioning member is guided in the specially shaped insert, the consequence of which is that, when the tensioning member is subjected to tension during operation, said tensioning member, guided by the specially shaped insert, is able to exert its effect on the kneecap without being able in any way to move laterally in relation to the kneecap. Thus, the specially shaped insert itself is involved in exerting a displacement force acting on the kneecap.

The object of the invention is to render superfluous the transfer of the displacement force from the tensioning member to the specially shaped insert. The object of the invention is achieved in that the tensioning member is attached to the overlay in such a manner that, during bending of the knee joint and stretching of the overlay, the tensioning member displaces the kneecap.

Owing to the fact that the tensioning member is attached to the overlay covering the specially shaped insert, said overlay, being a key component of the knee-joint bandage, is responsible for guiding the tensioning member and therefore also for exerting the displacement force on the kneecap, with the result that the specially shaped insert is able to maintain its positioning, which is essentially defined by the overlay, without being directly displaced by the tensioning member during tensioning thereof. Furthermore, the combination of tensioning member and overlay results in an essential advantage with regard to manufacture. Namely, the embedding of the tensioning member in the specially shaped insert represents a problem from the manufacturing viewpoint inasmuch as such specially shaped inserts are formed in an injection-moulding operation in which the tensioning member, integrated into the material of the specially shaped insert, must then simultaneously be included. The attachment of the tensioning member directly to the overlay represents a simple manufacturing operation which can be accomplished, for example, by glueing the tensioning member to the overlay, this being unproblematic from the manufacturing viewpoint for the reason that the corresponding side of the overlay is initially freely available when the components of the knee-joint bandage are being joined together.

There are various possibilities for attaching the tensioning member to the overlay. A preferred possibility consists in glueing the tensioning member to the overlay. Of course, sewing is also possible.

In order, during bending of the knee, to prevent creasing in the knee joint, such creasing being unpleasant for the wearer of the bandage, it is advantageous for a highly elastic gusset to be incorporated into the textile material of the bandage opposite the specially shaped insert in the region of the hollow of the knee. Such a gusset is stretched when the knee is extended and contracts again when the knee is bent, without there being any significant creasing.

The knee-joint bandage can be further improved with regard to its usability in that, in the region between the specially shaped insert and the edge of the bandage pointing towards the foot, a further highly elastic gusset is incorporated into the textile material of the bandage. Such a highly elastic gusset makes it easier for the knee-joint bandage to be pulled over the heel, because, during the thereby necessary extension of the bandage, the highly elastic gusset allows itself to be stretched, as a result of which the bandage can be easily fitted over the foot and, more particularly, over the heel.

Illustrative embodiments of the invention are presented in the drawings, in which.

Figure 1:
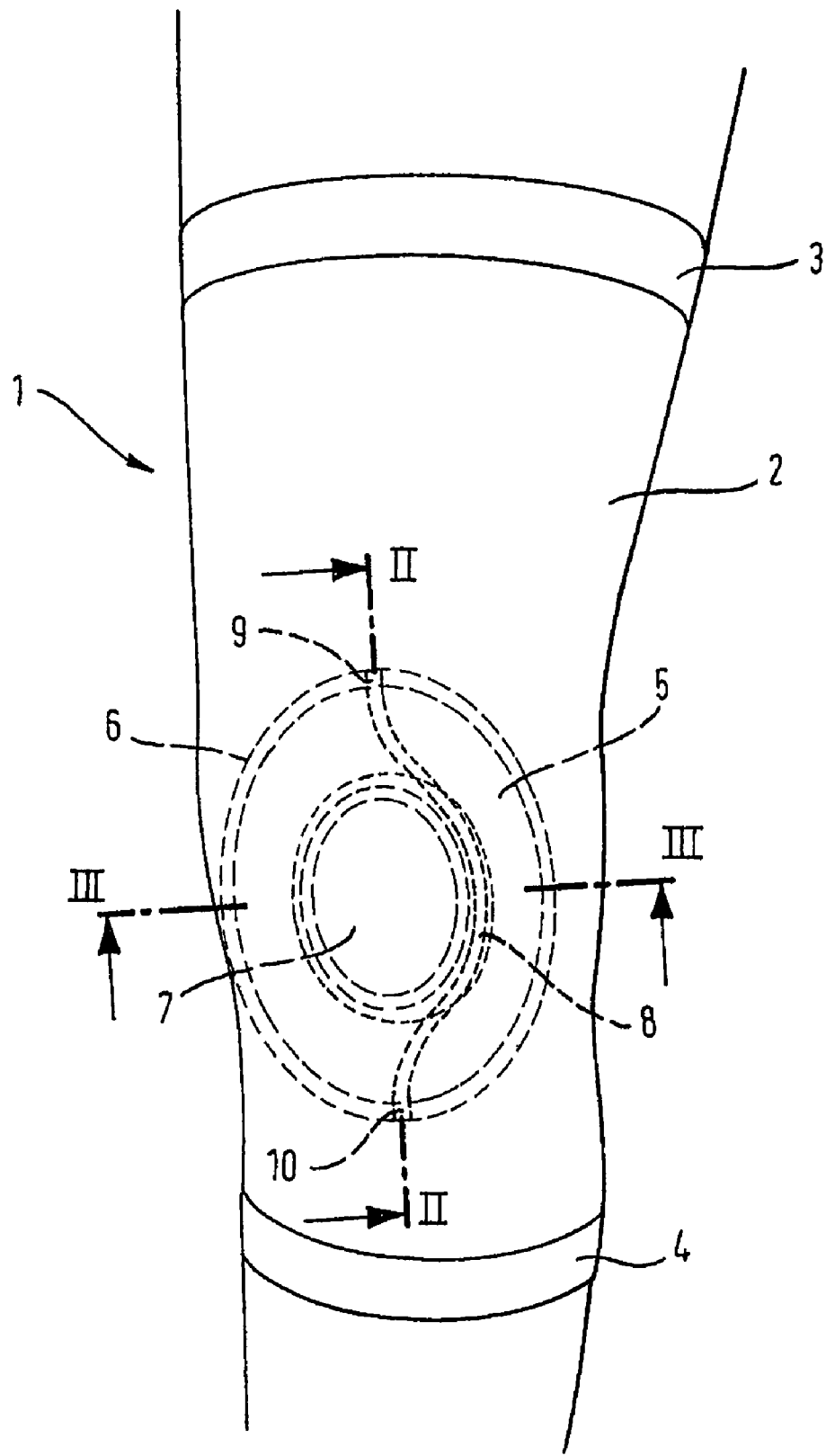
FIG. 1 shows a top plan view of the knee with the knee-joint bandage fitted.

The knee-joint bandage 1 presented in FIG. 1 consists of the stocking 2 which is made of elastic textile material and which is provided at its two ends with the two edges 3 and 4, said edges 3 and 4 helping to stop the bandage 1 from slipping. Furthermore, said edges 3 and 4 are made of a material of lower tension than the stocking 2, so as not to cut excessively into the wearer's leg at the respective locations. Incorporated into the stocking 2 on the front side of the knee joint is the specially shaped insert 5, which may be made, for example, of foam plastic or silicone and which is of considerable elasticity. Said specially shaped insert 5 is covered on the inside of the stocking 2 by the overlay 6, which is connected at its edges to the stocking 2, for example by glueing. The specially shaped insert 5 is provided with a central cutout into which, for example, the kneecap 7 fits. Consequently, the kneecap 7 is surrounded by the specially shaped insert 5. To this extent, the present knee-joint bandage is a knee-joint bandage of known design, of the kind presented in the initially mentioned DE 38 38 576.

As will also become apparent from the below-explained sectional drawings presented in FIGS. 2 and 3, the stocking 2 is provided in the region of the specially shaped insert 5 with the tensioning member 8, which is here in the form of a flexible, non-expandable textile strip. The tensioning member 8 is attached to the overlay 6, with the result that it follows all changes in position of the overlay 6. When the knee joint is bent (see FIG. 4), this results in a distance between the two ends 9 and 10 of the tensioning member 8, this leading to a stretching of the position of the tensioning member 8 as presented in FIG. 1. As a result of this stretching, the tensioning member 8 then exerts a pressure on the kneecap 7, which is surrounded by the specially shaped insert 5, said pressure suitably displacing the kneecap 7 in the desired manner. This effect is more fully discussed in the aforementioned DE 38 38 576 A1 with reference to FIGS. 3 and 4 thereof.

A particularly advantageous form of attachment of the tensioning member 8 to the overlay 6 consists in that the tensioning member is glued to the overlay 6, it being possible for the tensioning member 8 to be glued both on the side of the overlay 6 facing the leg and also on the side of the overlay 6 facing away from the leg. It should, however, be pointed out that it is, of course, also possible for the tensioning member to be attached in a different manner, for example by means of sewing.

Figure 2:
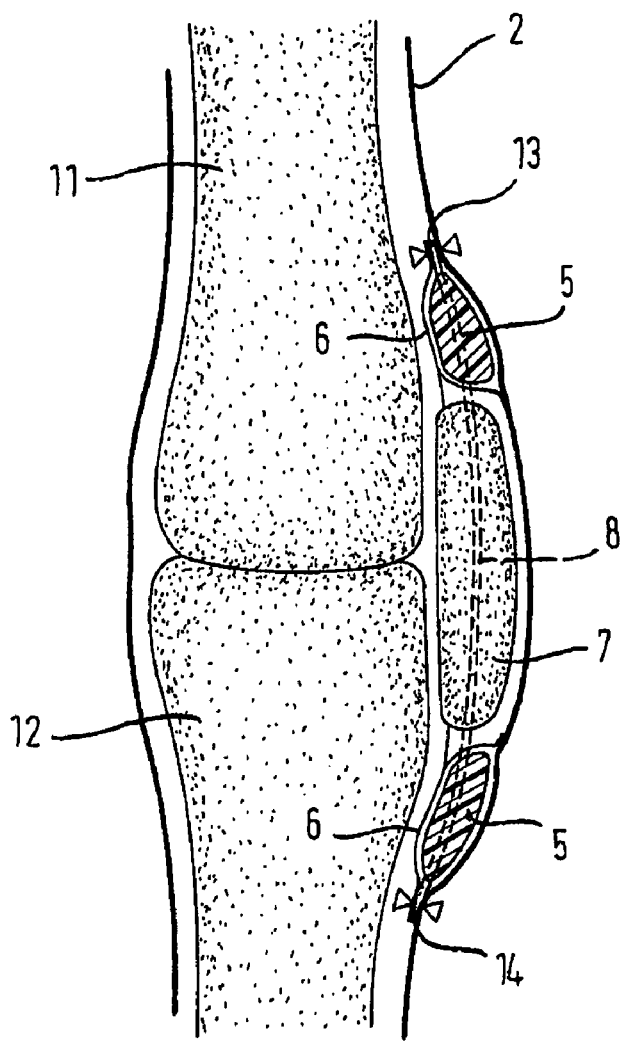
FIG. 2 shows the knee with the knee-joint bandage fitted, in a section along line II-II from FIG. 1.

FIG. 2 presents a section along line II-II from FIG. 1 and shows the femur 11 and the tibia 12, in front of the point of articulation of which is shown the kneecap 7. The stocking 2 is pulled over the knee joint and encloses the knee joint on all sides. Shown in the region of the kneecap 7 and surrounding the latter is the specially shaped insert 5, which is disposed on the inside of the stocking 2 and is covered by the overlay 6 on the side facing the knee joint. The overlay 6 is attached to the stocking 2 in the manner of a ring. The two outer attachment points shown in the sectional drawing in FIG. 2 are identified by reference numbers 13 and 14. Also attached at said attachment points 13 and 14 is the tensioning member 8, which is attached over its entire length to the overlay 6 and which, therefore, is co-tensioned when the overlay 6 is tensioned. At said attachment points 13 and 14 it is also possible, if desired, to apply an additional force, e.g. by means of straps, in order to provide the tensioning member 8 with additional tension, the tensioning member 8 then exerting the displacement forces which were explained in connection with FIG. 1.

Figure 3:
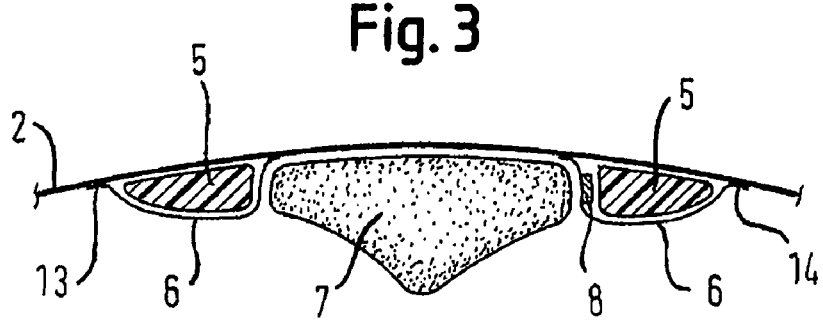
FIG. 3 shows a section along line III-III from FIG. 1.

FIG. 3 presents the corresponding portion of the knee-joint bandage 1 in a sectional drawing along line III-III. FIG. 3 shows the stocking 2 and, attached thereto, the overlay 6 with the attachment points 13 and 14 (see FIG. 2). The overlay 6 includes the ring-shaped specially shaped insert 5, which, in turn, surrounds the kneecap 7. Attached to the inside of the overlay 6 is the tensioning member 8, which extends in the longitudinal direction of the leg, as was explained with reference to FIG. 1. Consequently, a tensioning of the overlay 6 owing to bending of the respective knee is transferred directly to the tensioning member 8, which then exerts its displacement forces in the direction of the kneecap 7.

Figure 4:
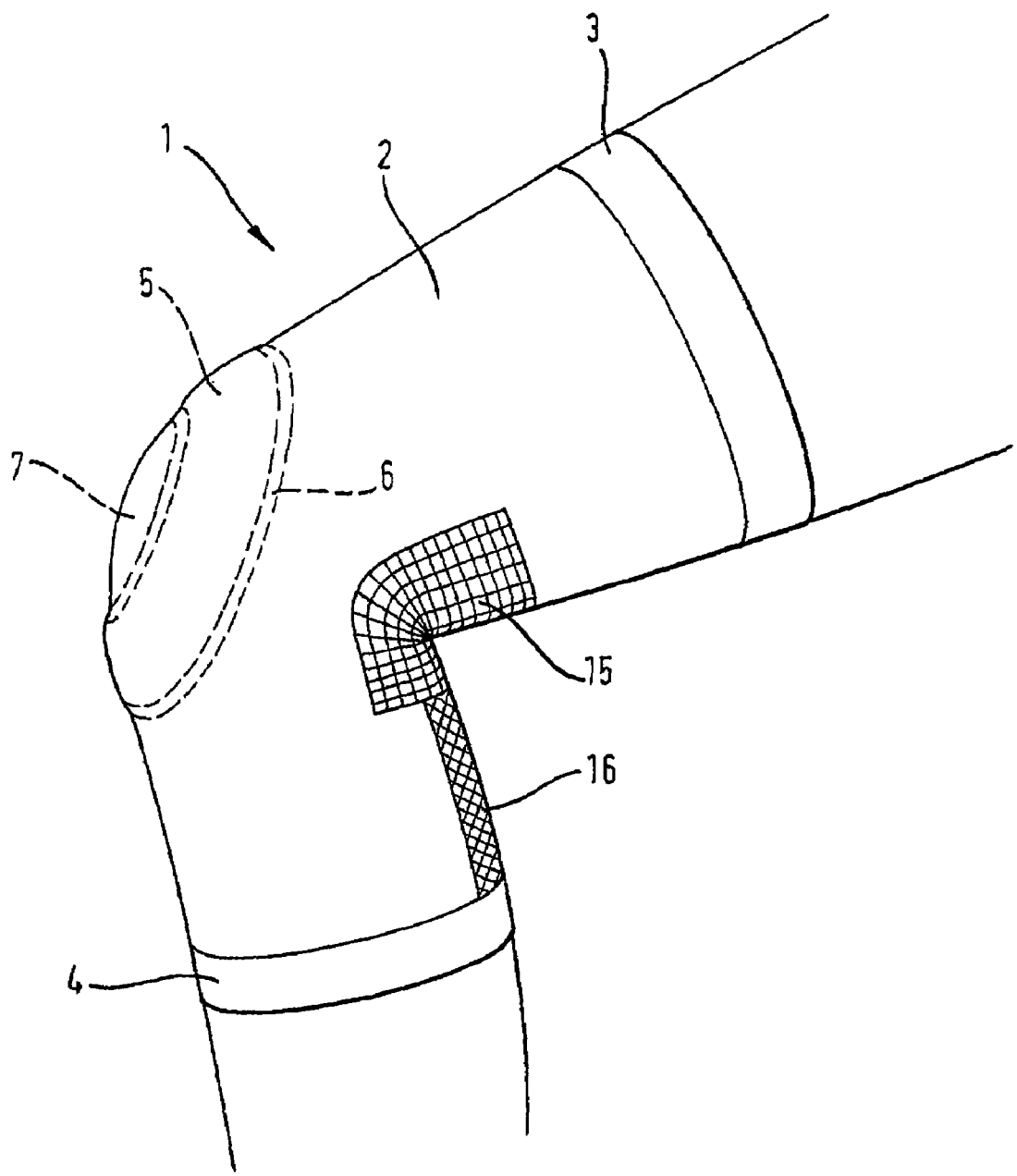
FIG. 4 shows a side view of a bent knee with the knee-joint bandage fitted.

FIG. 4 presents the knee-joint bandage 1 when fitted to a bent knee. Incorporated into the stocking 2 of the knee-joint bandage in the region of the hollow of the knee opposite the specially shaped insert 5 is the highly elastic gusset 15, which provides the stocking 2 with particular elasticity in this region. Said gusset 15 ensures that, during extending and bending of the knee, there is no creasing in the knee joint and that, during extending of the knee, there is a particular tension in the stocking, with the result that the knee joint can be bent and extended without hindrance.

The knee-joint bandage presented in FIG. 4 additionally contains, directly next to the highly elastic gusset 15 in the direction of the foot, a further highly elastic gusset 16, the purpose of which is to make it easier to fit the knee-joint bandage 1, more particularly to pull the knee-joint bandage 1 over the heel. During such fitting, there is particular stretching of the region 16, which, however, owing to its high elasticity, then correspondingly contracts again after fitting in the region of the knee joint.

What is claimed is:

1. Knee-joint bandage of elastic textile material, comprising:
    an inside of said knee-joint bandage being provided with a specially shaped insert having a ring-shape adapted for surrounding the kneecap in a cutout,
    an inner side of said specially shaped insert being covered by an overlay of identical or similar textile material attached to said textile material, the specially shaped insert being positioned adjacent to a separate flexible, non-expandable single piece tensioning member, a portion of said tensioning member being adapted to be positioned adjacent to connecting regions of the kneecap poles on the fibula side in an arc around the kneecap such that, when the distance between said connecting regions increases during bending of the knee joint, the distance of the arc from the connecting line between the kneecap poles is reduced and the tensioning member presses on the adjacent side of the kneecap, medially displacing and centering the latter,
    wherein the single piece tensioning member is attached over its entire length to the overlay in such a manner that, during bending of the knee joint and stretching of the overlay, the tensioning member displaces the kneecap.

2. Knee-joint bandage according to claim 1, wherein the tensioning member is glued to the overlay.

3. Knee-joint bandage according to claim 1, wherein opposite the specially shaped insert in a region of a hollow of the knee, a highly elastic gusset is incorporated into the textile material of the bandage.

4. Knee-joint bandage according to claim 3, wherein directly next to the highly elastic gusset in a direction of a foot, a second highly elastic gusset is incorporated into the textile material of the bandage.

5. Knee-joint bandage according to claim 2, wherein opposite the specially shaped insert in a region of a hollow of the knee, a highly elastic gusset is incorporated into the textile material of the bandage.

* * * * *

UNITED STATES PATENT AND TRADEMARK OFFICE Certificate

Patent No. 7,517,331 B2

Patented: April 14, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Holger Reinhardt, Kempen (DE); Heinrich Hess, Kleinblittersdorf (DE); Hans B. Bauerfeind, Zeulenroda (DE); Wolfgang Krause, Hofbieber (DE); and Rainer Scheuermann, Raisdorf (DE).

Signed and Sealed this Twenty-seventh Day of March 2012.

PATRICIA BIANCO
*Supervisory Patent Examiner*
Art Unit 3772
Technology Center 3700